United States Patent
Syed (10) Patent No.: US 11,172,948 B2
(45) Date of Patent: Nov. 16, 2021

(54) ARTERIAL EMBOLUS RETRIEVER

(71) Applicant: Mubin I. Syed, Springfield, OH (US)

(72) Inventor: Mubin I. Syed, Springfield, OH (US)

( * ) Notice: Subject to any disclaimer, the term of this patent is extended or adjusted under 35 U.S.C. 154(b) by 184 days.

(21) Appl. No.: 16/422,185

(22) Filed: May 24, 2019

(65) Prior Publication Data

US 2019/0357926 A1    Nov. 28, 2019

Related U.S. Application Data

(60) Provisional application No. 62/676,770, filed on May 25, 2018.

(51) Int. Cl.
| | |
|---|---|
| *A61B 17/221* | (2006.01) |
| *A61B 34/00* | (2016.01) |
| *A61B 17/22* | (2006.01) |
| *A61B 17/00* | (2006.01) |

(52) U.S. Cl.
CPC ............ *A61B 17/221* (2013.01); *A61B 34/73* (2016.02); *A61B 2017/00876* (2013.01); *A61B 2017/2215* (2013.01); *A61B 2017/22038* (2013.01); *A61B 2017/22079* (2013.01); *A61B 2217/005* (2013.01)

(58) Field of Classification Search
CPC .......... A61B 17/221; A61B 2017/2215; A61B 2017/22079; A61B 2017/22038; A61B 17/22031; A61B 34/73; A61B 2017/00876; A61B 2017/306; A61B 2016/00867; A61B 2016/22079; A61B 2217/005; A61F 2/011; A61F 2002/9528

USPC ........................................................ 606/127
See application file for complete search history.

(56) References Cited

U.S. PATENT DOCUMENTS

| | | | |
|---|---|---|---|
| 8,298,244 B2 | 10/2012 | Garcia et al. | |
| 8,685,039 B2 * | 4/2014 | Little ................... | A61B 17/221 606/127 |
| 8,784,441 B2 | 7/2014 | Rosenbluth et al. | |
| 9,161,766 B2 | 10/2015 | Slee et al. | |
| 9,408,626 B2 | 8/2016 | Tekulve | |
| 9,526,865 B2 | 12/2016 | Quick | |
| 9,597,171 B2 | 3/2017 | Shrivastava et al. | |
| 9,717,519 B2 | 8/2017 | Rosenbluth et al. | |
| 9,801,643 B2 | 10/2017 | Hansen et al. | |
| 10,085,759 B2 * | 10/2018 | Ciulla .................... | A61M 1/84 |
| 10,517,617 B2 * | 12/2019 | Aklog ............... | A61B 17/3207 |
| 2007/0138915 A1 | 6/2007 | Mulvihill et al. | |
| 2008/0269774 A1 * | 10/2008 | Garcia ................ | A61B 17/221 606/127 |

(Continued)

*Primary Examiner* — Tan-Uyen T Ho
*Assistant Examiner* — Bridget E. Rabaglia
(74) *Attorney, Agent, or Firm* — Jennifer Hayes; Nixon Peabody LLP (57) ABSTRACT

An arterial embolus retrieval system that includes an outer sheath configured as a tubular structure and that is able to move independent of a vessel wall. The arterial embolus retrieval system includes a retriever within the outer sheath, and configured to move independent of the outer sheath. The arterial embolus retrieval system also includes a handle configured to deploy the retriever, and a guidewire opposite of the handle and surrounded by the vessel wall. The outer sheath and the retriever can be configured to be guided to a location of an embolus using the guidewire. The guidewire can be configured to be retrieved once the outer sheath and the retriever are proximal to the embolus.

14 Claims, 5 Drawing Sheets

(56) References Cited

U.S. PATENT DOCUMENTS

| | | | |
|---|---|---|---|
| 2009/0192485 A1* | 7/2009 | Heuser | A61B 17/221 |
| | | | 604/500 |
| 2013/0289578 A1* | 10/2013 | Noriega | A61B 17/221 |
| | | | 606/127 |
| 2014/0257245 A1 | 9/2014 | Rosenbluth et al. | |
| 2017/0325931 A1 | 11/2017 | Bonnette et al. | |
| 2018/0235743 A1* | 8/2018 | Farago | A61M 39/22 |

* cited by examiner

ARTERIAL EMBOLUS RETRIEVER

CROSS REFERENCE TO RELATED APPLICATIONS

This application claims priority under 35 U.S.C. § 119 to U.S. Provisional Application No. 62/676,770, entitled "ARTERIAL EMBOLUS RETRIEVER," filed on May 25, 2018. The contents of that application are hereby incorporated by reference in their entirety.

TECHNICAL FIELD

The present disclosure relates to an apparatus for an arterial embolus retrieval system. Specifically, the present disclosure discloses a catheter-based retrieval device configured to remove an embolus in a human artery.

BACKGROUND

An embolism is a substance, which has dislodged from one site and traveled through a body's vascular circulation until the substance becomes lodged in a smaller vessel. The lodging of the substance within the smaller vessel can impede the flow of blood or other fluids within the smaller vessel. The embolism can cause partial or total blockage (a vascular occlusion) of blood flow in the affected vessel.

The partial or total blockage can affect a part of the body distant from the origin of the embolus. This can result in arterial occlusion, ischemia and potentially infarction. There are several different types of substances, or emboli. These can include blood clots, cholesterol plaque or crystals, fat globules, gas bubbles, and foreign bodies. Common results of arterial emboli include strokes and acute lower limb ischemia. In some less frequent circumstances, emboli can target the upper extremities, including mesenteric or renal arteries.

Arterial emboli require immediate treatment. The type of treatment depends upon the location and nature of the emboli. Typical treatment includes medication administered intravenously or intra-arterially using a catheter. Types of medication includes thrombolytics, anticoagulants, anti-platelet, etc. However, many patients are ineligible for such therapy as the medicine often takes a prolonged time for the treatment to be effective. Furthermore, these known medication can cause hemorrhaging.

Other solutions for removing arterial emboli include suction embolectomy and/or mechanical embolectomy. Mechanical embolectomy typically includes using different kinds of balloons, suction, or retrieval assemblies (e.g., stent retriever or snare). Typical embolectomy procedures include known shortcomings, risks and drawbacks. Embolectomy balloon catheters require open surgical excision upstream (typically at the groin artery or common femoral artery) to remove the embolus. In some cases, the deflated balloon catheter may not be able to get past the embolus to pull it out after it has been inflated.

Furthermore, suction catheter embolectomy does not work for hardened emboli. The mechanical assemblies can cause the embolus to fragment and to become dislodged from the original site. As a result, vascular occlusion becomes a frightening possibility in other parts of vascular circulatory system. Also, stent retriever devices are not typically effective for hardened emboli. Snare devices may not be able to grasp the embolus. As a result, there is a need for a more optimal embolus removal system.

SUMMARY

An arterial embolus retrieval system is disclosed. The arterial embolus retrieval system can include an outer sheath configured as a tubular structure and that is able to move independent of a vessel wall. The arterial embolus retrieval system includes a retriever within the outer sheath, and configured to move independent of the outer sheath. The arterial embolus retrieval system also includes a handle configured to deploy the retriever, and a guidewire extending from the proximal end towards a distal end of the arterial embolus retrieval system. The outer sheath and the retriever can be configured to be guided to a location of an embolus using the guidewire.

In some embodiments, the outer sheath is made up of a flexible material. In some embodiments, the retriever is configured to alternate between a deployed state and an undeployed state. The retriever is configured to move within the outer sheath to the location of the embolus in the undeployed state.

In some embodiments, the guidewire is configured to be positioned in place while an embolectomy is performed. The retriever can include an expansile cone. In some embodiments, the arterial embolus retrieval system can include a suction port located at the handle and configured to attach to a mechanical or manual vacuum. The manual vacuum can include a syringe inserted into the suction port at the handle.

In some embodiments, the retriever includes at least two prongs attached to the at least two prong ports. The ends of the at least two prongs include magnetic tips. In some embodiments, the expansile cone includes four prongs. Each of the four prongs comprises a magnetic tip. In some embodiments, the retriever, the expansile cone, and the at least two prongs includes a shape memory material. The magnetic tips of the at least two prongs are configured to lock together. The at least two prongs are expanded up to 8-10 mm when the at least two prongs are deployed. In some embodiments, the retriever is configured to advance out of the outer sheath when the guidewire is retracted.

In some embodiments, the retriever is configured to be advanced by manipulating the handle mechanism. In some embodiments, the guidewire is configured to be retracted once the outer sheath and the retriever are proximal to the embolus.

A second arterial embolus retrieval system is disclosed. The arterial embolus retrieval system can include an outer sheath configured as a tubular structure and that is able to move independent of a vessel wall. The arterial embolus retrieval system includes a retriever within the outer sheath, and configured to move independent of the outer sheath. The arterial embolus retrieval system also includes a handle configured to deploy the retriever.

Additional features and advantages of the disclosure will be set forth in the description that follows, and in part, will be obvious from the description, or can be learned by practice of the principles disclosed herein. The features and advantages of the disclosure can be realized and obtained by means of the instruments and combinations particularly pointed out in the appended claims. These and other features of the disclosure will become fully apparent from the following description and appended claims, or can be learned by the practice of the principles set forth herein.

BRIEF DESCRIPTION OF THE DRAWINGS

In order to describe the manner in which the above-recited disclosure and its advantages and features can be obtained, a more particular description of the principles described above will be rendered by reference to specific examples illustrated in the appended drawings. These drawings depict only example aspects of the disclosure, and are therefore not to be considered as limiting of its scope. These principles are described and explained with additional specificity and detail through the use of the following drawings.

DETAILED DESCRIPTION

The present disclosure provides an apparatus for an embolus retrieval system. The arterial embolus retrieval system can include an outer sheath, that is configured as a tubular structure that is able to move independent of a vessel wall. The arterial embolus retrieval system can also include a retriever within the outer sheath, and configured to move independent of the outer sheath. The arterial embolus retrieval system can include a handle configured to deploy the retriever, and a guidewire opposite of the handle and surrounded by the vessel wall. The outer sheath and the retriever can be configured to be guided to a location of an embolus using the guidewire. Furthermore, the guidewire can be configured to be retrieved once the outer sheath and the retriever are proximal to the embolus.

Figure 1:
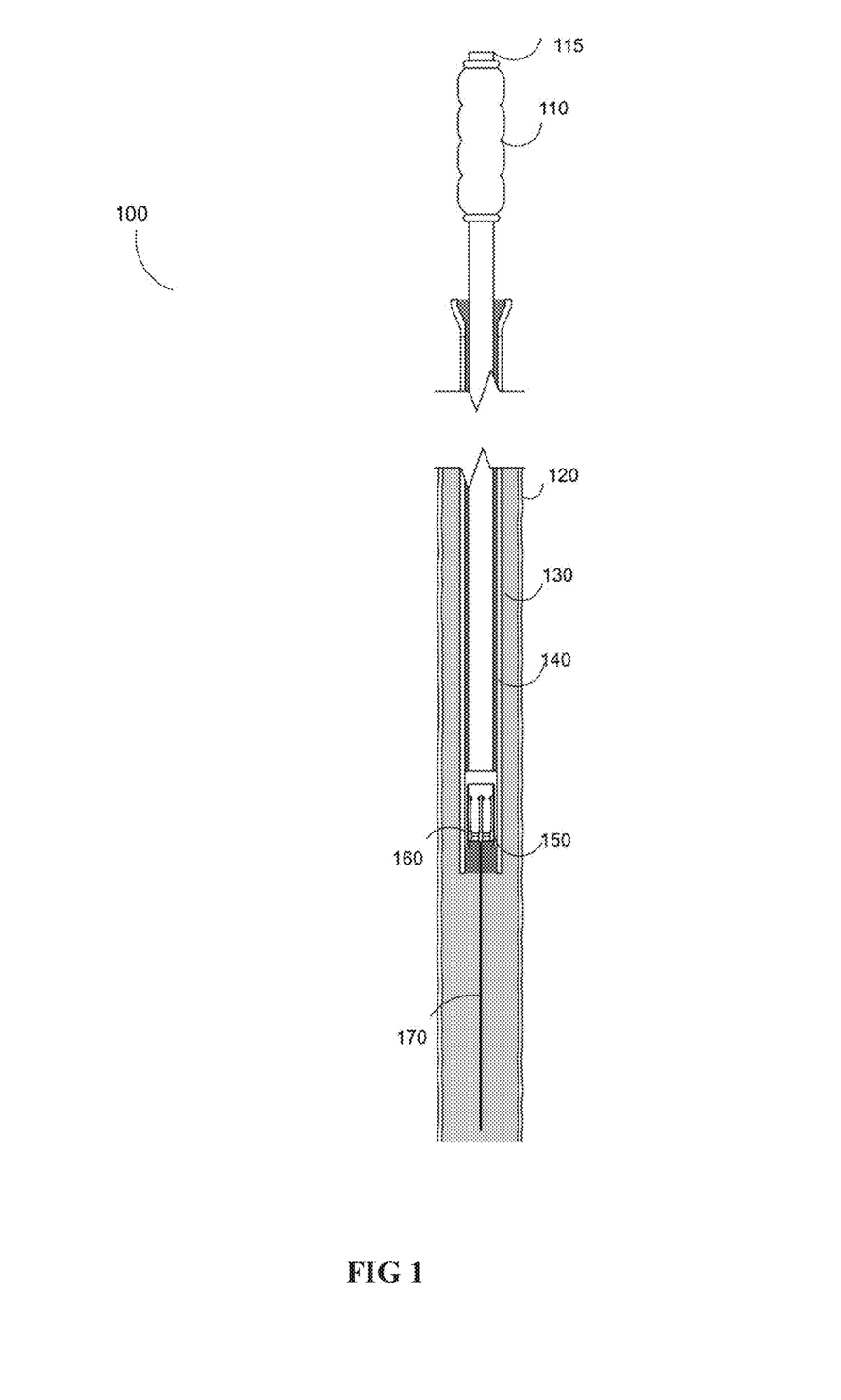
FIG. 1 illustrates a schematic view of the arterial embolus retrieval system, in accordance with an embodiment of the present disclosure.

FIG. 1 shows a schematic view of an arterial embolus retrieval system 100. The arterial embolus retrieval system 100 includes an outer sheath 130 and a retriever 140. In some embodiments, the outer sheath 130 includes a tubular shape that allows it to move independent of the vessel wall 120. The retriever 140 is configured to move within the outer sheath 130, independent of the outer sheath 130. The arterial embolus retrieval system 100 also includes a handle 110, located outside of the vessel wall 120, and configured to deploy the retriever 140 and all of its components. This is discussed in greater detail below. The arterial embolus retrieval system 100 can also include a guidewire 170. The guidewire can extend through the arterial embolus retrieval system 100, from the proximal end to the distal end. In some embodiments, the outer sheath 130 has a length between 190 to 210 cm, and a diameter of 5 to 6 Fr ID (French scale Inner Diameter) for tibial arteries. For larger vessels, the diameter of the outer sheath 130 is up to 8 Fr ID. Larger vessels can be found, for example, at the knee or higher. An example of a larger vessel includes the popliteal artery.

At one end, the guidewire 170 is typically inserted into a human body at a predetermined location. Specifically, the location for percutaneous insertion of the arterial embolus retrieval system 100 is often determined based on the embolus location. In some embodiments, the percutaneous insertion occurs within a common femoral artery. Other locations in the vascular circulatory system for percutaneous insertion is determined by the embolus location, access to the embolus location, and/or other health related factors of a patient. The opposing end of the guidewire 170, extending through the handle 110, remains outside of the patient's body.

In some embodiments, the outer sheath 130 is fabricated with a flexible material. Once inserted into the patient's body, the outer sheath 130 and the retriever 140 are guided to the embolus location using the guidewire 170. In some embodiments, the guidewire 170 is retrieved once the outer sheath 140 and the retriever 140 are proximal or near the location of the embolus. The retriever 140 is proximal to the embolus where the retriever is able to effectively grasp or attach to the embolus to perform an embolectomy. This is described in further detail below.

In another embodiment, the guidewire 170 is guided to the embolus location and is maintained at that location during the embolectomy. In some embodiments, the outer sheath 130 is advanced up to 15 mm from the embolus during the embolectomy. The retriever 140 is configured to alternate between a deployed state and an undeployed state, as further discussed below.

FIG. 1 illustrates the retriever 140 in an undeployed state. The undeployed state is also referred to as the compressed state. In the undeployed state, the retriever 140 is configured to move within the outer sheath 130, independent of the outer sheath 130. Once positioned at the embolus location the retriever 140 and the expansile cone 150 can transition to the deployed state. As illustrated in FIG. 1, the expansile cone 150 is retracted within the retriever 140 in the undeployed state. It should be understood that the expansile cone 150 is compressed within the retriever 140 when the retriever 140 is in the undeployed state.

Figure 2:
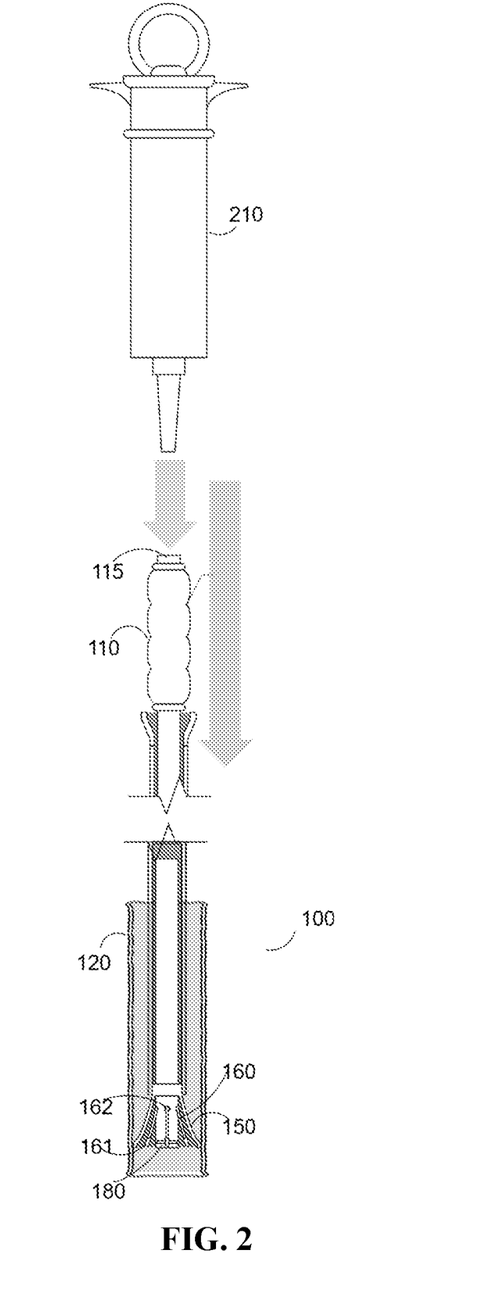
FIG. 2 illustrates a retriever deployed and an illustration of a manual suction embolectomy, in accordance with an embodiment of the present disclosure.

FIG. 2 illustrates the arterial embolus retrieval system 100 in the deployed state. FIG. 2 also illustrates a manual suction embolectomy, in accordance with an embodiment of the present disclosure. As an initial matter, the handle 110 is configured to be advanced and maneuvered by a technician. By maneuvering the handle 100, the arterial embolus retrieval system is positioned/repositioned and can be advanced further into the body.

In one embodiment, the handle 110 includes an input (not shown) which deploys the retriever 140. The input can be a mechanical input, such as a button, a switch, a lever, or any other mechanical input devices. For example, the retriever 140 can be deployed through a spring-like mechanism or a sliding lever mechanism. Either mechanism can be configured within the handle 110. Alternatively, the input can be an electrical or digital input device. The handle 110 also includes a port 115 that can be used to attach a vacuum. This is discussed in further detail below. The retriever assembly 140 is advanced by manipulating the handle 110.

In one embodiment, the retriever assembly 140 advances out of the outer sheath 140 when the guidewire 170 is retracted.

The expansile cone 150 includes a suction port 180 and grasping prong ports 162. The grasping prong ports 162 surround the suction port 180. The suction port 180 is used in a suction embolectomy procedure. For example, the suction port 180 is used with either a mechanical device or a manual device to perform the suction embolectomy. In some embodiments, a syringe is used to manually create a suction for the suction embolectomy. In some embodiments, the retriever includes prongs 160, which extend from the grasping prong ports 162. Each of the prongs 160 can include a magnetic tip 161. In some embodiments, the magnetic tips 161 allow for a firm grasping of the embolus, which prevents any further distal embolization by the fragmentation of the embolus. In an alternative embodiment, the expansile cone 150 includes the prongs 160, each with an associated magnetic tip 161. The magnetic tips 161 allow for a firmer grasping of the emboli without the embolus being fragmented.

In some embodiments, the expansile cone 150 maintains an angle of exit for the prongs 160 so as to avoid an inadvertent puncture of the vessel wall. In some embodiments, the expansile cone 150 is deployed before the prongs 160. When the expansile cone 150 reaches the vessel walls 120, the prongs 160 are deployed. In this way, the expansile cone 150 serves as a guide for the prongs 160 to pass the vessel walls 120 and around the embolus. In some embodiments, the deployment of the prongs 160 is automatic.

In some embodiments, the retriever 140 is used without the expansile cone 150. For example, the embolus is captured by the prongs 160 without the guide of the expansile cone 150. In this case, the prongs 160 can be made of a shape memory polymer, such as Nitinol. The prongs 160 exit the prong ports 162 in an arc-like configuration. In this example, the magnetic tips 161 of each prong 160 are blunt so as to not risk puncturing the wall of the blood vessel.

In some embodiments, the retriever 140 advances out of the outer sheath 130 when the guidewire (not shown) is retracted. Referring momentarily to an alternative embodiment illustrated in FIG. 5, the retriever 140 is advanced towards an embolus (not shown) while the guidewire 170 is still in position. The retriever 140 is advanced using the handle mechanism (shown in FIG. 2). In some embodiments, the retriever 140, expansile cone 150, and prongs 160 is made of a material that exhibits a shape memory effect. For example, the retriever 140, expansile cone 150 and prongs 160 is made of Nitinol or other shape memory polymers. It should be understood by one of ordinary skill in the art that shape memory effect materials (SMMs) are able to recover their original shape in the presence of an appropriate stimulus. Alloys such as Nitinol, return to their original shape and also exhibit suitable biocompatibility. Referring back to FIG. 2, the expansile cone 150 is deployed or expanded to the diameter of the vessel wall 120 upon advancing the retriever 140.

In some embodiments, a suction embolectomy is performed on the embolus. The arterial embolus retrieval system 100 includes a syringe 210 configured to provide suction to retrieve the embolus in combination with the retriever 140. In some embodiments, the syringe 210 is configured as a 60 cc syringe. The syringe 210 is inserted into the port 115 of the handle 110. Using the syringe 210, the suction port 180 is occluded by the embolus. In some embodiments, the suction port 180 extends through the entire length of the retriever 140 and is coupled to the handle port 115. When the suction port 180 is occluded by the embolus, the prongs 160 are deployed. In some embodiments, the guidewire (not shown) is retracted while the retriever 140 is deployed. The expansile cone 150 is also deployed and expanded to the vessel walls 120. As discussed above, in some embodiments, the expansile cone 150 is deployed before the prongs 160 to guide the prongs 160 to the embolus. When fully deployed, the expansile cone 150 expands up to 3 mm. While FIG. 2 illustrates a manual vacuum (syringe 210), in some embodiments, mechanical or electromechanical devices are used to create a vacuum force.

Figure 3:
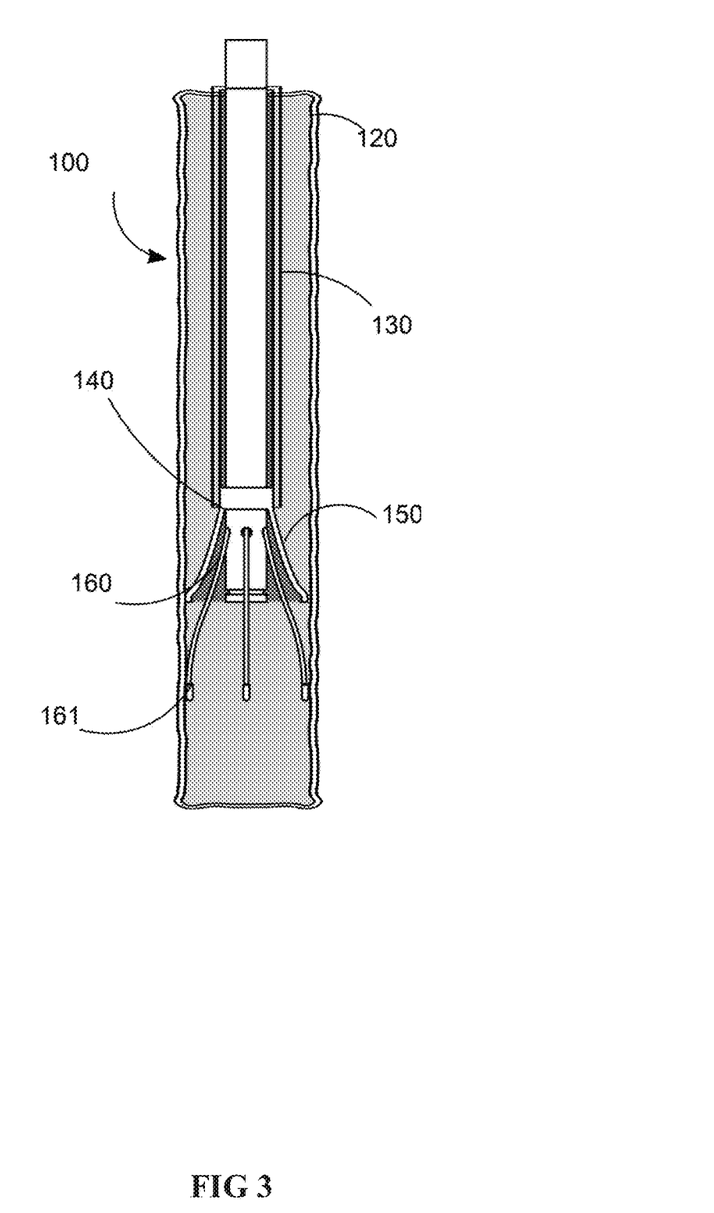
FIG. 3 illustrates grasping prongs being deployed over an embolus, in accordance with one embodiment of the disclosure.
Figure 5:
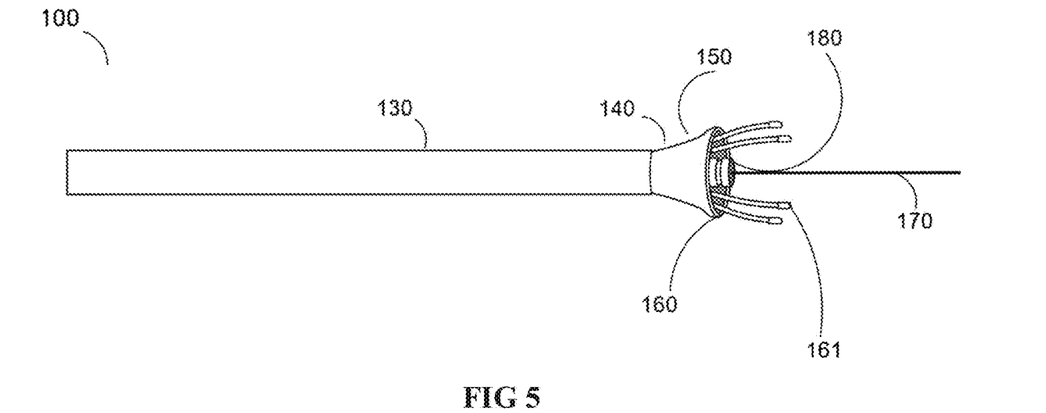
FIG. 5 illustrates an isometric view of the arterial embolus retrieval system, in accordance with one embodiment of the disclosure.

FIG. 3 illustrates the grasping prongs 160 being deployed over an embolus (not shown), in accordance with one embodiment of the disclosure. As discussed above, the prongs 160 are made of shape memory materials. The prongs 160 include an arc shape that enables the prongs 160 to extend despite the vessel walls 120. In some embodiments, the prongs 160 extend to cover the embolus. In alternative embodiments, the prongs 160 extend such that the magnetic tips 161 grasp the embolus. The prongs 160 are advanced from the prong ports 162. In some embodiments, the prong ports 162 are configured to cause the prongs 160 to deform upon being deployed. After deployment from the prong ports 162, the prongs 160 will return to their arc shape. In some embodiments, the prongs 160 are pre-curved (made of Nitinol and having thermal memory). The shape of the prongs 160 allow them to be deployed to capture the embolus without puncturing the vessel wall 120. As illustrated in FIG. 5, the grasping prongs are partially deployed.

Figure 4:
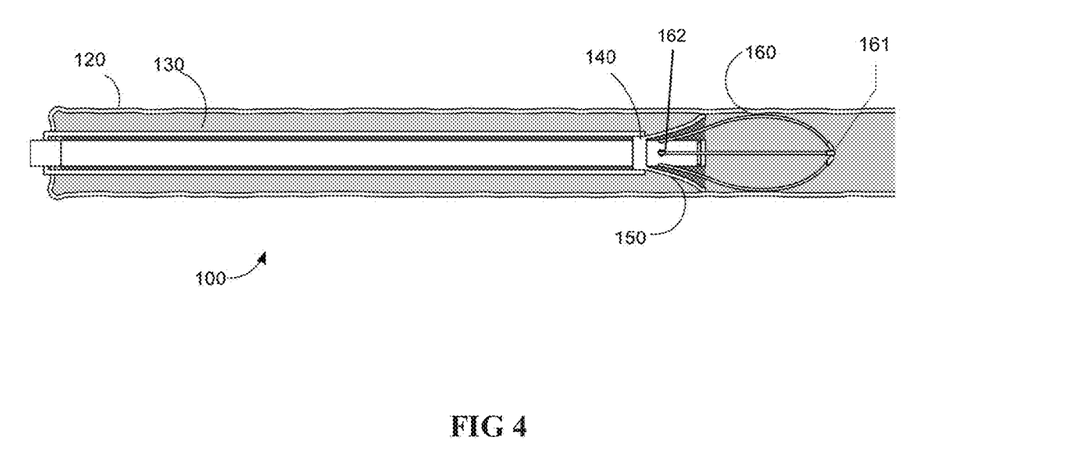
FIG. 4 illustrates the grasping prongs fully deployed, in accordance with one embodiment of the disclosure.

FIG. 4 illustrates the grasping prongs fully deployed, in accordance with embodiments of the disclosure. When the prongs 160 are fully deployed, the magnetic tip 161 of each prong 160 locks together. The locking of each of the magnetic tips 161 forms a firm grasp. The arc shape of the prongs 160 and the magnetic tips 161 enable the arterial embolus retrieval system 100 to firmly grasp the embolus. Firmly grasping the embolus prevents any further embolization and safely retrieves the embolus.

Figure 6:
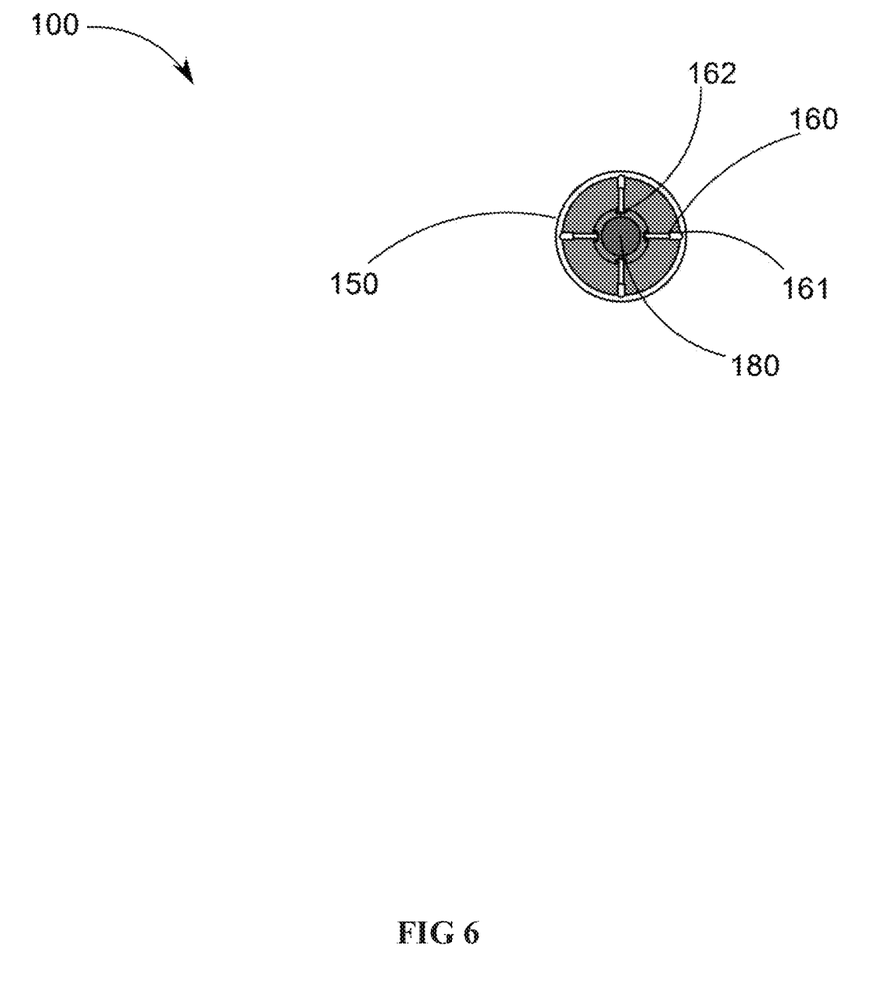
FIG. 6 illustrates an end view of the arterial embolus retrieval system, in accordance with an embodiment of the disclosure.

FIG. 6 illustrates an end view of the arterial embolus retrieval system 100, in accordance with embodiments of the disclosure. Once the embolus (not shown) is firmly grasped by grasping prongs 160 (i.e. prongs are locked together), the retriever (shown in FIG. 2) is retracted using the handle (shown in FIG. 2). During this procedure, suction is simultaneously applied via the suction port 180 alongside of the gripping of the grasping prongs 160. In some embodiments, the suction port 180 is between 0.5 to 2 mm. When fully deployed, the grasping prongs 160 expand between 8-10 mm.

It should be noted, that while the present disclosure discusses arterial emboli, the arterial embolus retrieval system 100 can be implemented to remove other terrestrial material, such as thrombi, foreign bodies, etc. The arterial embolus retrieval system can be configured such that it can be implemented with a variety of lumens within a patient.

While particular embodiments of the present invention have been shown and described, it will be obvious to those skilled in the relevant arts that changes and modifications may be made without departing from the invention in its broader aspects. Therefore, the aim in the appended claims is to cover all such changes and modifications that fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

The terminology used herein is for the purpose of describing particular embodiments only and is not intended to limit the invention. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

The invention claimed is:

1. An arterial embolus retrieval system comprising:
   an outer sheath comprising a tubular structure and configured to move independent of a vessel wall;
   a retriever comprising an expansile cone and at least four prongs attached to at least four prong ports, the retriever configured to move independent of the outer sheath, wherein ends of the at least four prongs include magnetic tips;
   a handle at a proximal end of the arterial embolus retrieval system and configured to deploy the retriever; and
   a guidewire extending from the proximal end towards a distal end of the arterial embolus retrieval system,
   wherein the outer sheath and the retriever are configured to be guided to a location of an embolus using the guidewire,
   wherein the retriever, expansile cone and at least four prongs comprise a shape memory material.

2. The arterial embolus retrieval system of claim 1, wherein the outer sheath comprises a flexible material.

3. The arterial embolus retrieval system of claim 1, wherein the retriever is configured to alternate between a deployed state and an undeployed state.

4. The arterial embolus retrieval system of claim 3, wherein the retriever is configured to move within the outer sheath to the location of an embolus in the undeployed state.

5. The arterial embolus retrieval system of claim 1, wherein the guidewire is configured to be positioned in place while an embolectomy is performed.

6. The arterial embolus retrieval system of claim 1, further comprising a suction port located at the handle and configured to attach to a mechanical or manual vacuum.

7. The arterial embolus retrieval system of claim 6, further comprising a syringe inserted into the suction port at the handle.

8. The arterial embolus retrieval system of claim 1, wherein the magnetic tips of the at least four prongs are configured to lock together and the at least four prongs are expanded up to 8-10 mm when the at least four prongs are deployed.

9. The arterial embolus retrieval system of claim 1, wherein the retriever is configured to advance out of the outer sheath when the guidewire is retracted.

10. The arterial embolus retrieval system of claim 1, wherein the retriever is configured to be advanced by manipulating the handle mechanism.

11. The arterial embolus retrieval system of claim 1, wherein the guidewire is configured to be retracted once the outer sheath and the retriever are proximal to the embolus.

12. An arterial embolus retrieval system comprising:
    an outer sheath comprising a tubular structure and configured to move independent of a vessel wall;
    a retriever configured to move independent of the outer sheath, wherein the retriever comprises an expansile cone and at least four prongs attached to at least four prong ports, wherein ends of the at least four prongs comprise magnetic tips; and
    a handle at a proximal end of the arterial embolus retrieval system and configured to deploy the retriever,
    wherein the retriever, expansile cone and at least four prongs comprise a shape memory material.

13. The arterial embolus retrieval system of claim 12, wherein the retriever is configured to alternate between a deployed state and an undeployed state, wherein the retriever is configured to move within the outer sheath to the location of an embolus in the undeployed state.

14. The arterial embolus retrieval system of claim 12, further comprising a suction port located at the handle and configured to attach to a mechanical or manual vacuum.

* * * * *